United States Patent [19]

Scanlon et al.

[11] Patent Number: 5,166,140

[45] Date of Patent: Nov. 24, 1992

[54] USE OF CERTAIN NUCLEOSIDE ANALOGS TO ATTENUATE CANCER CELL RESISTANCE TO DNA DAMAGING CHEMOTHERAPY

[75] Inventors: Kevin J. Scanlon, Pasadena; Lawrence C. Sowers, Duarte, both of Calif.

[73] Assignee: City of Hope, Duarte, Calif.

[21] Appl. No.: 421,342

[22] Filed: Oct. 13, 1989

Related U.S. Application Data

[63] Continuation-in-part of Ser. No. 234,096, Aug. 19, 1988, which is a continuation-in-part of Ser. No. 046,127, May 5, 1987, abandoned, which is a continuation-in-part of Ser. No. 352,994, May 17, 1989, Pat. No. 5,085,983.

[51] Int. Cl.$^5$ .................. A61K 31/70; A61K 31/52; A61K 31/505
[52] U.S. Cl. ........................................ 514/45; 514/46; 514/50; 514/261; 514/269
[58] Field of Search ............... 514/50, 45, 46, 261, 514/269

[56] References Cited

PUBLICATIONS

Kornberg, et al., "Studies on the Replication of DNA by DNA Polymerases" Cold Spring Harbor Symp. Quart. Biol. 28:9–19 (1963).

Newman, et al.,"Mechanisms of Cross-Resistance to Methotrexate and 5-fluorouracil in an A2780 Human Ovarian Carcinoma Cell Subline Resistant to Cisplatin", Biochemical Pharmacology 37:443–447 (1988).

Scanlon, et al, "Overexpression of DNA Replication and Repair Enzymes in Cisplatin-Resistant Human Colon Carcinoma HCT8 Cells and Circumvention by Azidothymidine", Cancer Communications 1(4):269–275 (1989).

Scanlon, et al., "Potentiation of Azidothymidine Cytotoxicity in Cisplatin-resistant Human Ovarian Carcinoma Cells", Cancer Communications 2(10):339–343 (1990).

Primary Examiner—John W. Rollins
Attorney, Agent, or Firm—Edward S. Irons

[57] ABSTRACT

A method involving the administration of nucleoside analogs to circumvent resistance attributable to the enhanced DNA repair capacity of cancer cells is described. The nucleoside analogs function as suicide substrates for DNA repair enzymes. A method of screening nucleoside analogs for utility as antitumor agents and a screening assay to individual recurrent tumors is described.

5 Claims, 1 Drawing Sheet

USE OF CERTAIN NUCLEOSIDE ANALOGS TO ATTENUATE CANCER CELL RESISTANCE TO DNA DAMAGING CHEMOTHERAPY

This application is a continuation-in-part of Ser. No. 234,096 filed Aug. 19, 1988 which is a continuation-in-part of Ser. No. 046,127 filed May 5, 1987, now abandoned. This application is also a continuation-in-part of Ser. No. 352,994 filed May 17, 1989, now U.S. Pat. No. 5,085,983 and of PCT/US89/03504 filed Aug. 16, 1989.

BACKGROUND OF THE INVENTION

The efficacy for cancer therapy of radiation and drugs, such as cisplatin, is often limited by the development of resistance. Biochemistry and tissue culture studies indicate that such resistance is a function of the capacity of cancer cells to repair damaged DNA. Parent application Ser. No. 234,096, in accord with various published papers, demonstrates enhanced expression of DNA repair enzymes by DNA resistant phenotypes of certain human carcinoma cell lines. See, e.g., Lai, G. M., et al., Biochem.Pharmacol. 37:4597-4600 (1988); Hospers, G.A.P., et al., Cancer Res. 48:6803-6807 (1988); Masuda, H., et al., Cancer Res. 48:5713-5716 (1988); Kraker, A., et al., Cancer Lett. 38:307-314 (1988); Scanlon, K. J., et al., Cancer Investigation 7:563-589 (1989) (in pressincorporated herein by reference); and Scanlon, K. J., et al., Anticancer Res. 9(#5) (September 1989) (incorporated herein by reference). See also, Murray, D., et al., Cancer Res. 45:6446-6452 (1985) and Miller, M. R., et al., J.Biol.Chem. 257:10204-10209 (1982).

AZT and various other nucleoside analogs are selective inhibitors of retroviral reverse transcriptases and of human DNA polymerases $\alpha$, $\beta$ and $\gamma$. See White, E. L., Biochem. and Biophys. Res. Comm. 161:393-398 (1989); Swinnen, L. J., et al., Cancer Res. 49:1383-1389 (1989); Ahnstrom, G., Biochimica et Biophysica Acta 1007:357-358 (1989); Elion, G. B., Science 244:41-47 (1989); Lin, T.-S., et al., J.Med.Chem. 32:1891-1895 (1989); Liu, S.-Y., et al., Cancer Res. 49:1366-1370 (1989); Ono, K., et al., Mol. Pharmacol. 35:578-583 (1989); Yarchoan, R., et al., New Eng.J.Med. 321:726-738 (1989) and U.S. Pat. No. 4,861,759.

SUMMARY OF THE INVENTION

This invention relates to the circumvention or amelioration of resistance attributable to an enhanced DNA repair capacity of cancer cells damaged by radiation or chemotherapy.

The parent application Ser. No. 234,096 states: "Properties that render human cancer cells resistant to chemotherapeutic drugs include enhanced expression of DNA repair enzymes and that new properties appear to enhance the sensitivity of the same cells to other drugs. For example, human leukemia cells resistant to cisplatin evidence enhanced sensitivity to dideoxy cytidine. Similarly, human ovarian cancer cells resistant to cisplatin have been shown to demonstrate increased sensitivity to AZT" (page 20, lines 8-14).

This phenomenon is observed because dideoxy cytidine (ddC), AZT and other nucleoside analogs are metabolized by cellular enzymes (kinases) to the triphosphates which serve as suicide substrates for DNA repair and replication enzymes, including among others DNA polymerase $\beta$. The consequent inhibition of DNA repair and replication enhances the cytotoxicity of radiation and DNA damaging chemotherapeutic agents in the resistant but not necessarily in the parental cell line.

The invention includes the discovery that the administration of certain nucleoside analogs, either alone or in combination with a DNA damaging agent such as radiation or cisplatin, avoids, ameliorates or circumvents human tumor cell resistance to such agents.

Another aspect of the invention includes a method for screening nucleoside analogs and derivatives thereof for utility as antitumor agents.

The invention also provides a screening assay to individual recurrent tumors, whereby the susceptibility of such individual tumors to a panel of candidate nucleotide analogs is determined. Detection of increased activity of these enzymes by the polymerase chain reaction (PCR) assay described in Ser. No. 234,096 allows for the design of specific nucleoside analogs.

DETAILED DESCRIPTION OF THE INVENTION

Figure 1:
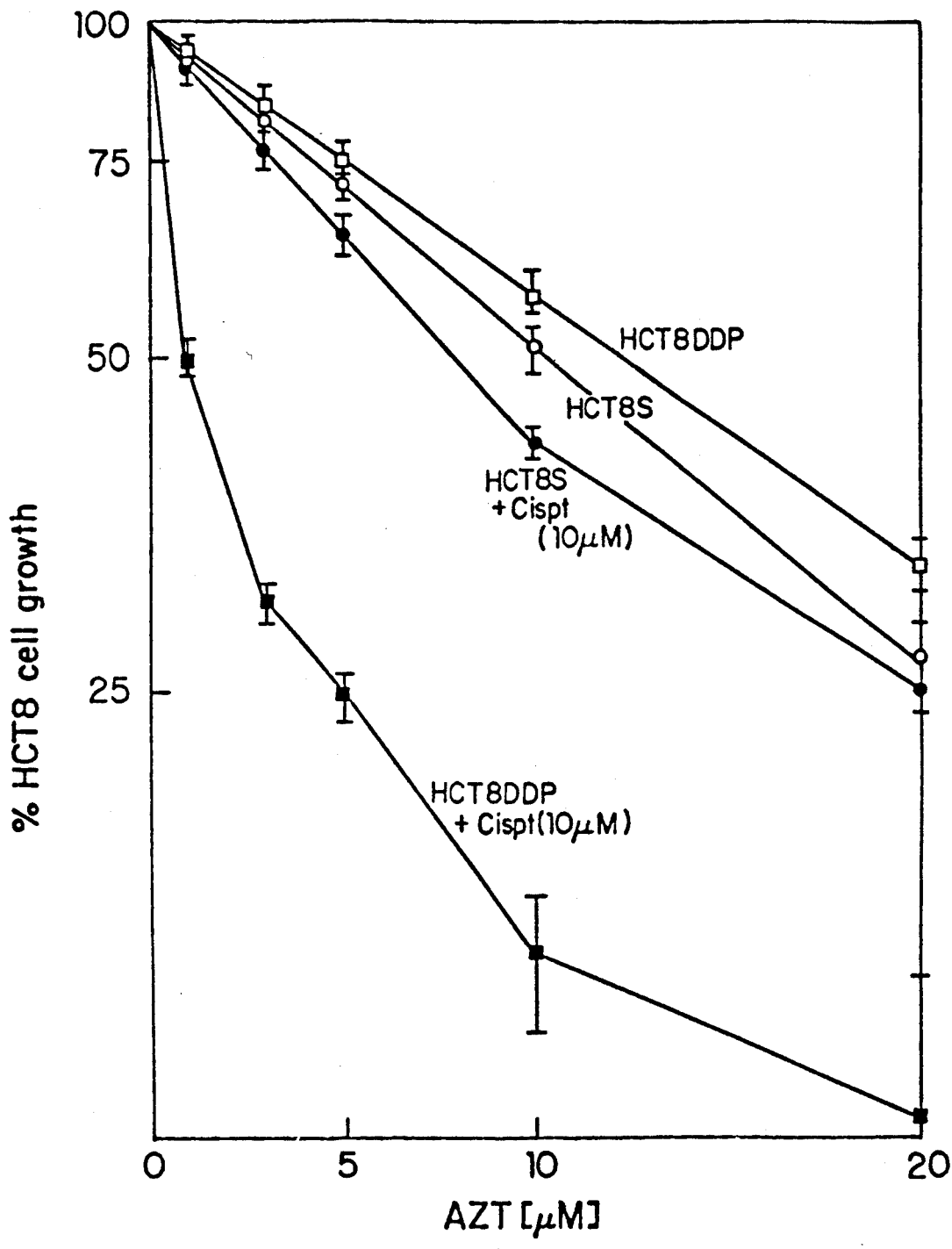
FIG. 1 illustrates the advantages which result from sequential treatment of cancer cells, first with cisplatin and then with AZT.

Some of the nucleoside analogs useful in this invention include those represented by Formula I and Formula II:

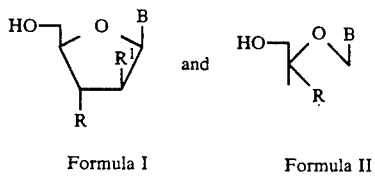

Formula I    Formula II in which B is adenine, thymine, cytosine, guanine, inosine or a heterocyclic compound derived therefrom such as 5-methylcytosine and one or both of R and $R^1$ are halogen, preferably fluorine or iodine, azide, amine, hydrogen or hydroxyl.

An important part of the invention entails a recognition of the interdependence of three factors to achieve amelioration or circumvention of resistance, namely (i) whether the cells are sensitive or resistant, and if resistant, the degree of resistance, (ii) the type of cancer cell involved and (iii) the sequence in which the DNA damaging agent and nucleoside analog are administered. By an appropriate regimen implementing the consequences of such interdependence, resistance to DNA damaging therapy may be effectively treated.

For example, in instances where a specific nucleoside analog may be ineffective with a specific type of cancer resistant cells, pretreatment of such cells with, e.g., cisplatin may result in an effective regimen.

Specific nucleoside analogs useful in the invention include, but are not limited to, 3' azido-2',3' dideoxythymidine (AZT), dideoxy inosine (DDI), each of the purine nucleosides described in U.S. Pat. No. 4,861,759, and Yarchoan, supra, and ganciclovir which, as the triphosphate, is a potent inhibitor of DNA poymerase $\alpha$.

Table I illustrates the efficacy of ganciclovir as a suicide substrate evidenced by its toxicity to cisplatin resistant and sensitive A2780 cell lines.

TABLE I

Cytotoxic Studies with Ganciclovir in Human Carcinoma Cells Sensitive ("S") and Resistant (DDP) to Cisplatin

| Cell Line | αDNA Polymerase Activity* | Ganciclovir EC$_{50}$ (μM) |
|---|---|---|
| A2780S | 95(±6.7) | 110(±2.1) |
| A2780DDP | 214(±8.1) | 30(±1.5) |
| HCT8S | 30.9(±4.1) | 60(±2.3) |
| HCT8DDP | 41.7(±4.4) | 40(±4.2) |

*The determination of DNA polymerase α was calculated as pmoles/10$^6$ cells/10 min (mean ± SD). The A2780 and HCT8 cells were plated in 35 mm petri dishes with RPMI 1640 nutrient. Twenty-four hours later, the cells were treated with 6 concentrations, of ganciclovir in saline. The concentrations were in equal increments from 1 micromolar to 100 micromolar. Six days later the cells were counted on a Coulter Counter. The experiment was done in triplicate.

As indicated in Table I, A2780 cells resistant to cisplatin are 3–4 fold more sensitive to ganciclovir. This correlates with an approximate 2 fold increase in DNA polymerase α levels. A similar but more modest effect is observed for HCT8 cell lines for both DNA polymerase α levels and changes in ganciclovir sensitivity.

Table II reflects inhibition of A2780 cell sensitive (S) and resistant (DDP) growth by Cisplatin AZT Ara A, Ara C, and ddC. The experiment was conducted in triplicate in the manner described with respect to Table I.

TABLE II

Inhibition of A2780 cell growth by cancer chemotherapeutic agents

| Compound | Treatment Time (hr) | EC$_{50}$ (μM)$^c$ A2780S | EC$_{50}$ (μM)$^c$ A2780DDP | Ratio$^a$ |
|---|---|---|---|---|
| Cisplatin | (1) | 7.0(±1.4)$^b$ | 90.0(±2.2)$^b$ | +12.8 |
| AZT | C.exp.* | 10.0(±1.1)$^b$ | 510.2(±11.1)$^b$ | +51.0 |
| araA | C.exp.* | 16.2(±2.4)$^b$ | 64.7(±6.1)$^b$ | +4.0 |
| araC | C.exp.* | 0.1(±0.01)$^b$ | 4.5(±0.5)$^b$ | +45.0 |
| ddC | C.exp.* | 1.5(±0.8)$^b$ | 4.0(±1.6)$^b$ | +2.6 |

$^a$Ratio of EC$_{50}$ of sensitive cells to that of resistant cells which denotes the degree of resistance of cross-resistance.
$^b$Mean ± SD
$^c$EC$_{50}$ is the concentration of drug that reduces cell proliferation by ½ during 6 days subsequent to an exposure with a cancer chemotherapeutic agent.
*C.exp. indicates continuous exposure.

The data in Table II indicates the degree of resistance is reduced by Ara A and ddC alone but increased by AZT and Ara C alone.

Table III illustrates the inhibition of A2780 cell growth by sequential treatment first with cisplatin and then with AZT, ddC and Ara A.

TABLE III

Inhibition of A2780 Cell Growth by Cancer Chemotherapeutic Agents.

| 1. Sequencing | EC$_{50}$ (μM)$^b$ A2780S | A2780DDP A2780DDP |
|---|---|---|
| (a) Cisplatin (1hr), washout, AZT | 7.0(+1.1)$^a$ | 10.0(+1.1)ab) |
| (b) Cisplatin (1 hr), washout, ganciclovir | 64.0 | 30.0 |
| (c) Cisplatin (1 hr), washout, ddC | 0.2(+0.02)$^a$ | 3.0(+0.1)$^a$ |
| (d) Cisplatin (1 hr), washout, araA | 8.5 | 30.0 |

$^a$Mean + SD
$^b$EC$_{50}$ is the concentration of drug that reduces cell proliferation by ½ during 6 days subsequent to an exposure with a cancer chemotherapeutic agent.

A2780 cells were well-plated (35 mm ..dishes) and 24 hours later the cells were treated with cisplatin for 1 hr., washed out and then treated with 6 concentrations of from 1 μM to 100 μM increased in equal increments of a nucleoside analog in saline. Cells were then washed and incubated for 6 days. The cells were counted on a Coulter Counter and the experiment was done in triplicate.

As Table III also indicates, synergistic combinations are provided by administration of the nucleoside analogs of the invention sequentially with cisplatin or radiation. The combination of cisplatin and AZT is representative. AZT is a thymidine derivative metabolized via the thymidine metabolic pathway. The triphosphate AZTTP acts as a suicide substrate by causing DNA chain termination. See, White, E. L., Biochem. and Biophys. Res. Comm. 161:393–398 (1989).

Cisplatin cells are collaterally resistant to AZT alone and to the TTP antimetabolites. Increased TTP levels in cisplatin resistant cells results in a competitive disadvantage for AZTTP incorporation. To remove DNA adducts, resistant phenotype cells such as HCT8 cells resistant to cisplatin apparently metabolize their DNA more rapidly than sensitive cells. Repair gaps following cisplatin adduct removal provide sites for the incorporation of suicide substrates such as AZTTP. Sequential treatment of cancer cells, first with cisplatin and then AZT, enhances the reduction in cell growth. The exposure first to cisplatin enhances the capacity of the cells to synthesize and repair DNA damage which is then exploited by the administration of the suicide substrate AZTTP. This phenomenon is illustrated by FIG. 1.

Any of the nucleoside analogs of this invention can be used in this sequential treatment protocol.

Table IV includes data further exemplifying the invention.

TABLE IV

| EC$_{50}$ (μM) | (C) ddA | (C) ddC | (C) ddG | (C) ddT | Pt+ ddc (C) | Pt+ AZT (C) | (C) AZT | (2h) Ara C | (1h) Cis Pt | (C) Cord-icpin | (C) Ribov-irin | (C) Acycl-ovir | (C) Gancy-clovir | (C) HU | (1h) DAUR |
|---|---|---|---|---|---|---|---|---|---|---|---|---|---|---|---|
| A2780S | 10(2) | 1.5(3) | 60 | 110 | 0.2 | 7(3) | 10(2) | 0.1(2) | 7 | 70 | 27(2) | >300 | 110 | 75 | 100 |
| A2780 DDP | 25 | 4(3) | 110 | >750 | 3(3) | 10(2) | 510(2) | 4.5(2) | 90 | 310 | 45(2) | >300 | 30 | 60 | 100 |
| MCF-7S | 30 | 2.5 | 210 | >500 | — | 6 | 65(2) | 2.5 | 15 | 130 | 100(2) | >300 | 200 | 100* | 58 |
| MCF-7 DDP | 30 | >100 | 180 | >500 | — | 0.5 | 10(2) | 5 | 35 | — | — | >300 | 50 | 200 | 85 |
| HCT8S | 33 | 2 | 35 | >150 | 0.4 | 6 | 5.5(2) | 29 | 30 | 110 | 70 | >300 | 60 | 100 | 11 |
| HCT8-DDP | 36 | 23 | 45 | >500 | 1.5 | 1 | 11(2) | 79 | 100 | 95 | 50 | >300 | 40 | 100 | 15 |
| K562S | 37.5(2) | 25 | 160 | >400 | — | — | 125(2) | 0.3 | 6 | 130(2) | 62(2) | >300 | 135(2) | 40 | 9 |
| K562-DDP | 28(2) | 5 | 190 | >400 | — | — | 150(2) | 0.3 | 15 | 160(2) | 75(2) | >300 | 295(2) | 140* | — |
| K562-ARAC | 36(2) | >300 | 150(2) | >400 | — | — | 70(2) | 8.0 | 25 | 67(2) | 42(2) | >300 | 150(2) | 40 | 10 |

TABLE IV-continued

| EC$_{50}$ ($\mu$M) | (C) ddA | (C) ddC | (C) ddG | (C) ddT | Pt+ ddc (C) | Pt+ AZT (C) | (C) AZT | (2h) Ara C | (1h) Cis Pt | (C) Cord- icpin | (C) Ribov- irin | (C) Acycl- ovir | (C) Gancy- clovir | (C) HU | (1h) DAUR |
|---|---|---|---|---|---|---|---|---|---|---|---|---|---|---|---|
| K562-VP16 | 35 | 100 | 170 | 200 | — | — | 200 | 8.0 | 15 | 150 | 55 | >300 | 250 | 40 | — |

*Slow growth

The data in Table IV indicates, inter alia, the following:
1. A2780: Ovarian carcinoma cells become resistant to cisPt, requiring >12 fold more cisPt.
CisPt resistant cells can be killed with 3.3 fold LOWER ganciclovir concentration (30 uM).
By using cisPt in combination with AZT, both cisPt resistant and sensitive cells can be killed with equal efficiency.
2. MCF7: Human breast cancer cells resistant to cisPt (by a factor of 2.3) are 4 fold MORE sensitive to ganciclovir and 6.5 fold more sensitive to AZT.
3. HCT8: Human colon cancer cells which have become 2.7 fold resistant to cisPt are 1.5 fold more sensitive to ganciclovir.
4. K562: Human leukemia cells resistant to cisPt are more sensitive to ddC by a factor of 5.
Human leukemia cells resistant to araC are 2 fold more sensitive to cordecepin and AZT.

The treatment of human patients is an important aspect of the invention. Preferably, an appropriate nucleoside analog is administered intravenously in a therapeutically effective amount, e.g., about 10 mg/kg body weight, while suspended or dissolved in an appropriate carrier such as water.

Serum levels of nucleoside analogs are achievable to micromolar range which is effective to kill resistant cells.

What is claimed is:

1. A method which comprises in vitro administration to viable human cancer cells which have acquired resistance to a DNA damaging chemotherapeutic agent, or methotrexate or radiation, a nucleoside analog of Formula I or Formula II, said nucleoside being metabolized by said cells to nucleoside triphosphates which are suicide substrates for a DNA repair or replication enzyme, and being administered in an amount therapeutically effective to inhibit the DNA repair function of such cells.

2. A method as defined by claim 1 in which said DNA damaging agent is cisplatin and in which said nucleoside analog is AZT or ganciclovir.

3. A method as defined by claim 1 in which said nucleoside analog is ganciclovir, AZT, Ara A, Ara C, or ddC and said enzyme is polymerase $\beta$.

4. A method which comprises in vitro administration to cisplatin resistant human tumor cells of ganciclovir, Ara A, Ara C, or ddC to such cells in an amount therapeutically effective to inhibit DNA polymerase $\beta$.

5. A method as defined by claim 4 in which said nucleoside analog is ganciclovir.

* * * * *